United States Patent [19]
Jalbert

[11] Patent Number: 5,686,111
[45] Date of Patent: Nov. 11, 1997

[54] ANIMAL FOOD SUPPLEMENT BRIQUETTE

[75] Inventor: Jacques Jalbert, Beaconsfield, Canada

[73] Assignee: Concentres Scientifiques Belisle Inc., St. Mathias, Canada

[21] Appl. No.: 433,975

[22] Filed: May 4, 1995

[30] Foreign Application Priority Data

May 4, 1994 [CA] Canada ................... 2122863

[51] Int. Cl.⁶ ................................................ A61K 9/14
[52] U.S. Cl. ................ 424/489; 424/438; 424/439; 424/442
[58] Field of Search .................. 127/41; 424/489, 424/438, 490, 439, 442; 426/2, 601

[56] References Cited

U.S. PATENT DOCUMENTS

| | | | |
|---|---|---|---|
| 3,658,549 | 4/1972 | Geiersberger et al. | 426/2 |
| 3,982,008 | 9/1976 | Amin | 426/2 |
| 4,263,052 | 4/1981 | Bichsel et al. | 127/41 |
| 5,211,980 | 5/1993 | Cox | 426/601 |

*Primary Examiner*—Thurman K. Page
*Assistant Examiner*—William E. Benston, Jr.
*Attorney, Agent, or Firm*—Eric Fincham

[57] ABSTRACT

There is disclosed an animal food supplement and a method and apparatus for preparing the same. The supplement is a high concentration vitamin/mineral supplement which is formed as a briquette by passing a mixture of the vitamin and minerals through a compacting step at a relatively low temperature.

5 Claims, 1 Drawing Sheet

ANIMAL FOOD SUPPLEMENT BRIQUETTE

BACKGROUND OF THE INVENTION

The present invention relates to animal food supplements and more particularly, relates to a method and apparatus for preparing animal food supplements.

The practice of preparing food supplements for animal feed is well known in the art and has been widely practiced. Initially, many of these food supplements were used as a general purpose "all in one" type of arrangement wherein many different ingredients were mixed together and used as an additive to the traditional feed. While this practice is still widely used, there has been an increasing desire for more specific types of additives. Thus, research has shown that both the diet and the use of food supplements may be varied depending on factors such as the type of animal to the season to the particular results desired. In other words, increasingly there is the need for very specific types of supplements for a given situation. For example, it has been traditional to use various cereal products in combination with certain mineral/protein/vitamin additives. However, there are objections to this arrangement since it does not provide the farmer with the opportunity to precisely control the diet of the animals.

Traditionally, the supplements have been provided in several different forms. They can either be provided as a loose mixture of the various ingredients, pelletized, or provided as a solid block. The loose mixture of the various ingredients is the least desirable since it becomes difficult to ensure that individual feedings contain an even mixture of all ingredients which are usually of different particle sizes. In order to manufacture the other forms, it becomes necessary to add various binding agents. Typically, these binding agents have been cereal and molasses or the like. One of the most widely accepted forms is the use of pellets.

Pellet mills operate by feeding the material to be pelleted to a compression side of a die over which an extrusion means operates to force the material through the die holes and through a discharge side of the die. The continuous stream of material from the die holes is then sub-divided to form individual pellets.

In the case of a high concentration vitamin/mineral supplement, the mixture becomes difficult to pelletize since it tends to be an abrasive mixture and it is also undesirable to have the vitamins pass through the die since they are subjected to a relatively high temperature (frequently over 100° C.) at which point in time some of the vitamins can lose some of their biological activity.

SUMMARY OF THE INVENTION

It is therefore an object of the present invention to provide for a method of compacting a mixture of vitamins/minerals at a low enough temperature to retain full biological activity of the vitamins.

It is a further object of the present invention to provide an animal food supplement which is in the form of a briquette and which has a high percentage of vitamin/mineral content therein.

According to the present invention, there is provided a process for the manufacture of animal feed supplements which includes the steps of mixing together a plurality of minerals and vitamins to form a composition, passing the composition between rolls having a plurality of pockets formed therein, and maintaining a pressure sufficient to briquette the composition while maintaining a temperature within the composition below 100° C.

In greater detail, there is provided an animal food supplement having a high percentage of minerals/vitamins therein, the supplement being in the form of briquets formed by passing the mixture through a compacting step.

The mixture itself may comprise different combinations of minerals, electrolytes and vitamins. Generally, the minerals will include those selected from calcium, phosphorous, magnesium, sulphur, potassium, sodium, cobalt, copper, iron, iodine, manganese, zinc, and selenium. Other elements may be included if desired.

The percentage of water will vary, between 2% to 10%. The phosphorous used in the process is preferably that of monodicalciumphosphate. This is advantageous for the practice of the invention as this can not normally be used in such mixtures which are subjected to pelletizing, rather, one must use a tripolyphosphate which has a lower biological activity. Similarly, the calcium has to be in a finer or more highly divided form for pelletizing. The previous mixtures tended to cause more pollution since many of the elements were required to be in such a fine form. In the practice of the present invention, the magnesium, or at least a portion thereof, is in the form of magnesium oxide which functions as a binder.

A critical element of the present invention is the processing of the mixture into briquets. This is accomplished at a temperature below 100° and preferably below 60° C. The prior art, using pelletizing, produces a temperature above 120° C. which causes some of the materials to loose their desirable biological activity. In other words, the vitamins will tend to suffer degradation due to heat during processing.

BRIEF DESCRIPTION OF THE DRAWING

Reference will now be made to the accompanying drawing of FIG. 1 which illustrates the practice of the invention.

DESCRIPTION OF THE PREFERRED EMBODIMENTS

Figure 1:
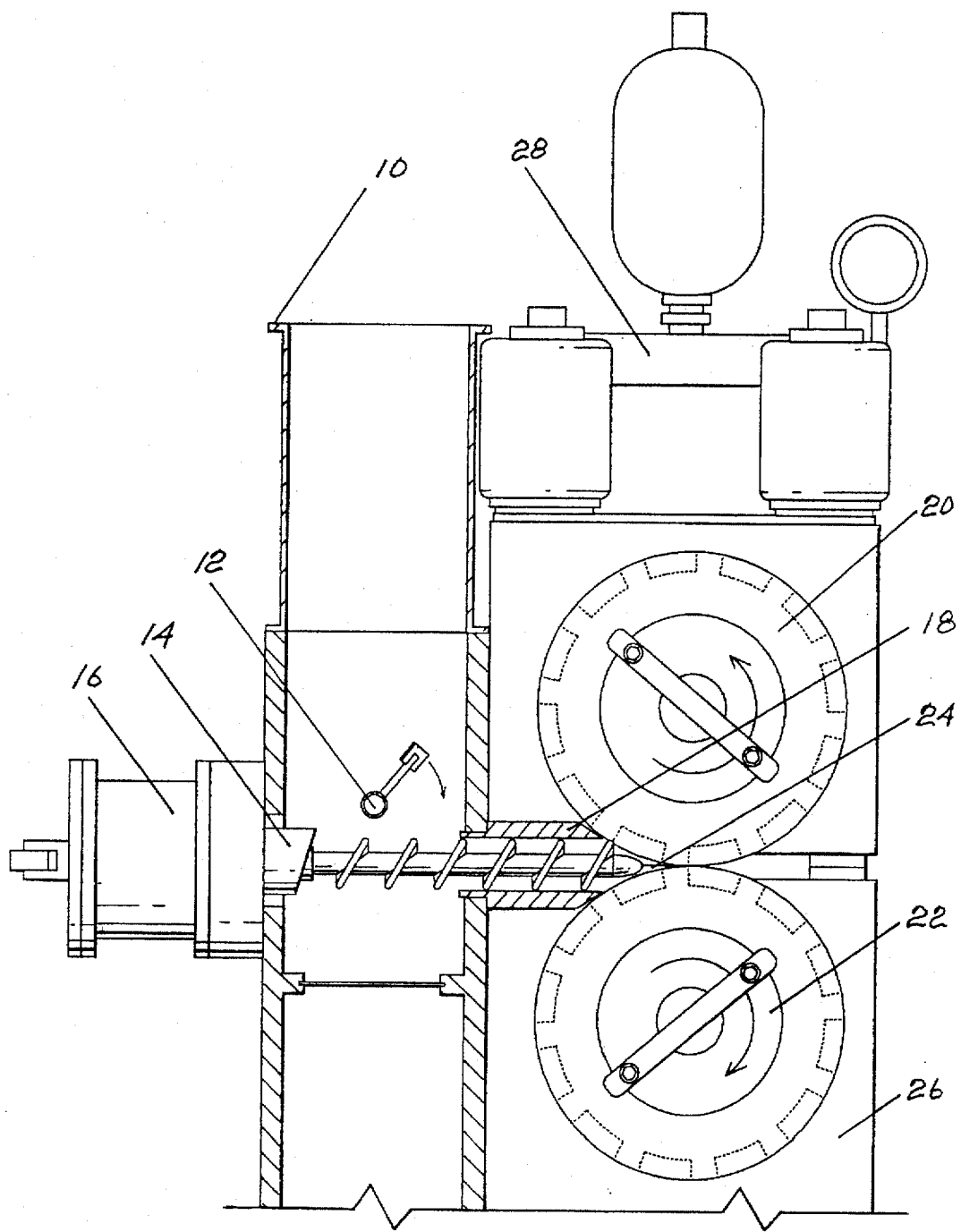

The apparatus is a briquetting type of system and thus includes a feed hopper 10 into which the composition to be briquetted is fed. A paddle mixer 12 is provided to ensure uniform distribution of the various ingredients. The composition is then fed to a screw feeder 14. As is conventional, screw feeder 14 is mounted in a screw feeder bearing block 16 and the composition is feed by screw feeder 14 through a housing or feed adaptor 18 to a pair of rolls 20 and 22. A cheek plate 24 is provided and rolls 20 and 22 are mounted in bearing blocks 26. A hydraulic system 28 is adapted to provide the necessary pressure for rolls 20 and 22.

The above system is adapted for briquetting and a plurality of recesses (not shown) are provided in rolls 20 and 22.

The following examples illustrate the practice of the invention.

| Batch Ingredients | | 1 | 2 | 3 | 4 | 5 | 6 | 7 |
|---|---|---|---|---|---|---|---|---|
| Calcium | % | 10 | 10 | 10 | 10 | 10 | 18 | 0 |
| Phosphorus | % | 10 | 10 | 10 | 10 | 10 | 6 | 14 |
| Magnesium | % | 6 | 6 | 6 | 6 | 6 | 4.5 | 6 |
| Sulphur | % | 3.25 | 3.25 | 3.25 | 3.25 | 3.12 | 2.5 | 3.25 |
| Potassium | % | 1 | 1 | 1 | 1 | 1 | 1 | 1 |
| Sodium | % | 11 | 11 | 11 | 11 | 11 | 9 | 10 |
| Water | % | 5 | 8.5 | 8.5 | 0 | 2.7 | 2.7 | 2.7 |
| Cobalt | mg/kg | 100 | 100 | 100 | 100 | 100 | 80 | 100 |
| Copper | mg/kg | 1000 | 1000 | 1000 | 1000 | 1000 | 800 | 1000 |
| Iron | mg/kg | 4200 | 4200 | 4200 | 4200 | 4200 | 2800 | 9600 |
| Flour max. | mg/kg | 750 | 750 | 750 | 750 | 750 | 430 | 1350 |
| Iodine | mg/kg | 120 | 120 | 120 | 120 | 120 | 96 | 120 |
| Manganese | mg/kg | 3800 | 3800 | 3800 | 3800 | 3800 | 3040 | 3800 |
| Zinc | mg/kg | 3800 | 3800 | 3800 | 3800 | 3800 | 3040 | 3800 |
| Selenium | mg/kg | 20 | 20 | 20 | 20 | 20 | 16 | 20 |
| Calcium Stearate | % | — | — | 0.3 | 0.5 | — | — | — |
| Mixing Time | Min. | 10 | 10 | 10 | 10 | 10 | 10 | 10 |
| Vit. A | U.I./kg | 500,000 | 500,000 | 500,000 | 500,000 | 500,000 | 400,000 | 500,000 |
| Vit. D | U.I./kg | 150,000 | 150,000 | 150,000 | 150,000 | 150,000 | 120,000 | 150,000 |
| Vit. E | U I./kg | 1500 | 1500 | 1500 | 1500 | 1500 | 1200 | 1500 |

| Tested Material | | Run No. 1 Batch 1 | Run No. 2 Batch 2 | Run No. 3 Batch 3 | Run No. 4 Batch 3 | Run No. 5 Batch 4 | Run No. 6 Batch 4 |
|---|---|---|---|---|---|---|---|
| Material Bulk Density | (g/cm3) | 1.06 | 1.07 | 1.06 | 1.06 | 1.03 | 1.03 |
| Roll Diameter | (mm) | 305 | 305 | 305 | 305 | 305 | 305 |
| No. of Pockets | | 66 | 66 | 66 | 75 | 75 | 75 |
| No. of Rows | | 3 | 3 | 3 | 2 | 2 | 2 |
| Pressure in Hydraulic Sys. | (MPa) | 13.75 | 8.25 | 6.75 | 6.75 | 6.25 | 13.00 |
| Initial Roll Gap | (mm) | 0.3 | 0.3 | 0.3 | 0.5 | 0.5 | 0.5 |
| Briquet Calc. Pressure | (MPa) | 185.79 | 113.29 | 95.16 | 161.15 | 145.80 | 299.28 |
| Briquet Temperature | (DEG.C) | N.M. | N.M. | N.M. | N.M. | N.M. | 40 |
| Briquet Weight | (g) | N.M. | N.M. | N.M. | N.M. | N.M. | 2.98 |
| Fines Percentage | (%) | N.D. | N.D. | N.D. | N.D. | N.D. | 12.9 |

| Tested Material | | Run No. 7 Batch 5 | Run No. 8 Batch 6 | Run No. 9 Batch 6 | Run No. 10 Batch 6 | Run No. 11 Batch 7 |
|---|---|---|---|---|---|---|
| Material Bulk Density | (g/cm3) | 1.04 | 1.14 | 1.14 | 1.14 | 0.95 |
| Roll Diameter | (mm) | 305 | 305 | 305 | 305 | 305 |
| No. of Pockets | | 75 | 75 | 75 | 75 | 75 |
| No. of Rows | | 2 | 2 | 2 | 2 | 2 |
| Pressure in Hydraulic Sys. | (MPa) | 13.00 | 13.75 | 16.50 | 20.75 | 20.75 |
| Initial Roll Gap | (mm) | 0.5 | 0.5 | 0.5 | 0.5 | 0.5 |
| Briquet Calc. Pressure | (MPa) | 299.28 | 314.63 | 383.69 | <475.78 | <475.78 |
| Briquet Temperature | (DEG.C) | 40 | 42 | 46 | 42 | 50 |
| Briquet weight | (g) | 4.17 | 3.42 | 4.62 | 3.14 | 2.51 |
| Fines Percentage | (%) | 11.2 | 7.8 | 12.5 | 12.3 | 10.1 |

N.M. Not Measured
N.D. Not Determined

In the above examples, the different minerals may be provided from varying sources thereof. These components are well known to those skilled in the art and may be selected from such well known compounds. For example, the minerals may be provided from, among others, calcium carbonate, monodicalcium phosphate, calcium phosphate, calcium chloride, calcium formate, monoamoniumphosphate, dicalciumphosphate, magnesium sulphate, sodium sulphate, potassium chloride, double sulphates of magnesium and potassium, etc.

As above mentioned, the various components can be selected from different sources providing the mineral/ vitamin. A typical formulation is given by way of example without being limited thereto and is as follows:

| | % by Weight |
|---|---|
| Calcium Carbonate | 26.0 |
| Dicalcium Phosphate | 42.6 |
| Salt | 18.1 |
| Magnesium oxide | 4.5 |
| Vitamins and micro-ingredients | 8.8 |

Vitamins and micro-ingredients include: Vitamin A, D and E; zinc oxide, manganous oxide, copper sulfate, EDDT, iron sulfate, sodium selenite and mineral oil.

The pressure, as above mentioned, will be sufficient to briquette the composition while maintaining the temperature below 100° and more preferably, below approximately 60° C. The pressure would normally vary between 6.25 MPa and 20.75 MPa.

I claim:

1. A process for the manufacture of animal feed supplements comprising the steps of mixing together a plurality of minerals and vitamins to form a composition, passing said composition between rolls having a plurality of pockets formed therein, maintaining a pressure sufficient to form briquettes while maintaining a temperature within said composition below 100° C.

2. The process of claim 1 wherein said composition is maintained at a temperature below about 60° C. while passing between said rolls.

3. The process of claim 1 wherein said minerals include calcium, phosphorus, magnesium, sulphur, potassium and sodium.

4. The process of claim 1 wherein said ingredients include calcium carbonate, calcium sulphate, calcium chloride, calcium formate, monoamoniumphosphate, dicalciumphosphate, magnesium sulphate, sodium sulphate, potassium chloride, double sulphates of magnesium and potassium, monodicalciumphosphate and magnesium oxide.

5. The process of claim 1 wherein said pressure is between 6.25 MPa and 20.75 MPa.

* * * * *